United States Patent
Hauger et al.

(10) Patent No.: US 10,582,856 B2
(45) Date of Patent: Mar. 10, 2020

(54) SURGICAL ASSISTANCE SYSTEM

(71) Applicant: Carl Zeiss Meditec AG, Jena (DE)

(72) Inventors: Christoph Hauger, Aalen (DE); Roland Guckler, Aalen (DE); Gerald Panitz, Ellwangen (DE)

(73) Assignee: CARL ZEISS MEDITEC AG, Jena (DE)

( * ) Notice: Subject to any disclaimer, the term of this patent is extended or adjusted under 35 U.S.C. 154(b) by 1036 days.

(21) Appl. No.: 14/631,319

(22) Filed: Feb. 25, 2015

(65) Prior Publication Data
US 2015/0250387 A1 Sep. 10, 2015

(30) Foreign Application Priority Data

Mar. 7, 2014 (DE) ........................ 10 2014 103 044

(51) Int. Cl.
*A61B 5/00* (2006.01)
*A61B 90/20* (2016.01)
(Continued)

(52) U.S. Cl.
CPC ........ *A61B 5/0084* (2013.01); *A61B 1/00009* (2013.01); *A61B 5/0035* (2013.01);
(Continued)

(58) Field of Classification Search
CPC ......... A61B 1/04; A61B 1/0005; A61B 90/36; A61B 50/13
See application file for complete search history.

(56) References Cited

U.S. PATENT DOCUMENTS

| | | | | |
|---|---|---|---|---|
| 5,098,426 A | * | 3/1992 | Sklar | ........................ A61F 9/008 219/121.6 |
| 6,661,571 B1 | * | 12/2003 | Shioda | ..................... A61B 1/04 359/368 |
| 2003/0137723 A1 | * | 7/2003 | Sander | .................... G02B 7/001 359/380 |
| 2004/0070822 A1 | | 4/2004 | Shioda et al. | |
| 2005/0033556 A1 | | 2/2005 | Miura | |

(Continued)

FOREIGN PATENT DOCUMENTS

| | | |
|---|---|---|
| DE | 10 2010 039 289 | 2/2012 |
| JP | 7-95556 | 4/1995 |
| WO | 2014/013412 | 1/2014 |

OTHER PUBLICATIONS

German Office Action dated Nov. 11, 2014.

*Primary Examiner* — Joseph M Santos Rodriguez
(74) *Attorney, Agent, or Firm* — Nixon Peabody LLP; Jeffrey L. Costellia

(57) ABSTRACT

A surgical assistance system includes an endomicroscope (4) and an imaging device (2) for capturing image data, and a transmission unit (63) for transmitting the image data. A pathology unit (70) includes a receiving unit (74) for receiving the image data and a display unit (76) displays the image data. A data connection (69) connects the transmission unit (63) to the receiving unit (74). The imaging device (2) and/or the endomicroscope (4) has at least one functional unit assigned to a functional control unit (65). A data receiving unit (64) receives data from the pathology unit (70). The pathology unit (70) has an input unit (77) for inputting functional control data for the functional control unit (65) and a transmitter unit (73) transmits the functional control data to the devices. The data receiving unit (64) receives and relays the functional control data to the functional control unit (65).

13 Claims, 5 Drawing Sheets

(51) Int. Cl.
  G06F 19/00 (2018.01)
  A61B 1/00 (2006.01)
  A61B 17/00 (2006.01)
  A61B 90/25 (2016.01)
  A61B 34/20 (2016.01)
  A61B 1/313 (2006.01)
(52) U.S. Cl.
  CPC .......... A61B 5/0071 (2013.01); A61B 5/0075 (2013.01); A61B 17/00234 (2013.01); A61B 90/20 (2016.02); G06F 19/3418 (2013.01); A61B 1/313 (2013.01); A61B 90/25 (2016.02); A61B 2017/00973 (2013.01); A61B 2034/2065 (2016.02); G06F 19/3481 (2013.01)

(56) References Cited

U.S. PATENT DOCUMENTS

| | | | |
|---|---|---|---|
| 2005/0254008 A1* | 11/2005 | Ferguson | A61B 3/1025 |
| | | | 351/205 |
| 2011/0090325 A1* | 4/2011 | Hauger | A61B 5/0261 |
| | | | 348/77 |
| 2011/0178395 A1 | 7/2011 | Miesner et al. | |
| 2011/0280810 A1 | 11/2011 | Hauger et al. | |
| 2012/0038761 A1 | 2/2012 | Sander | |
| 2013/0324846 A1 | 12/2013 | Yaroslavsky et al. | |
| 2014/0005555 A1 | 1/2014 | Tesar | |

\* cited by examiner

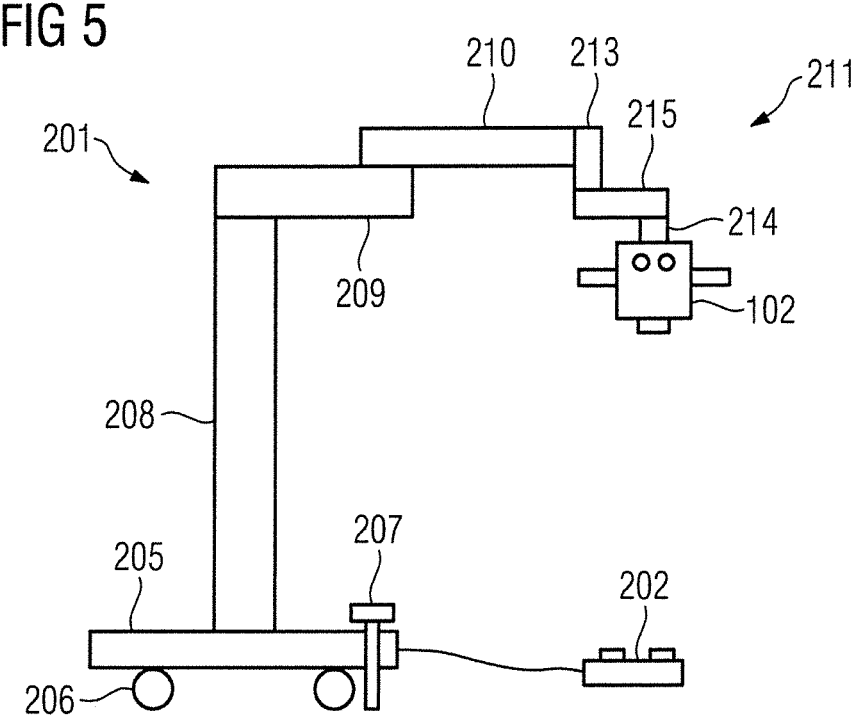
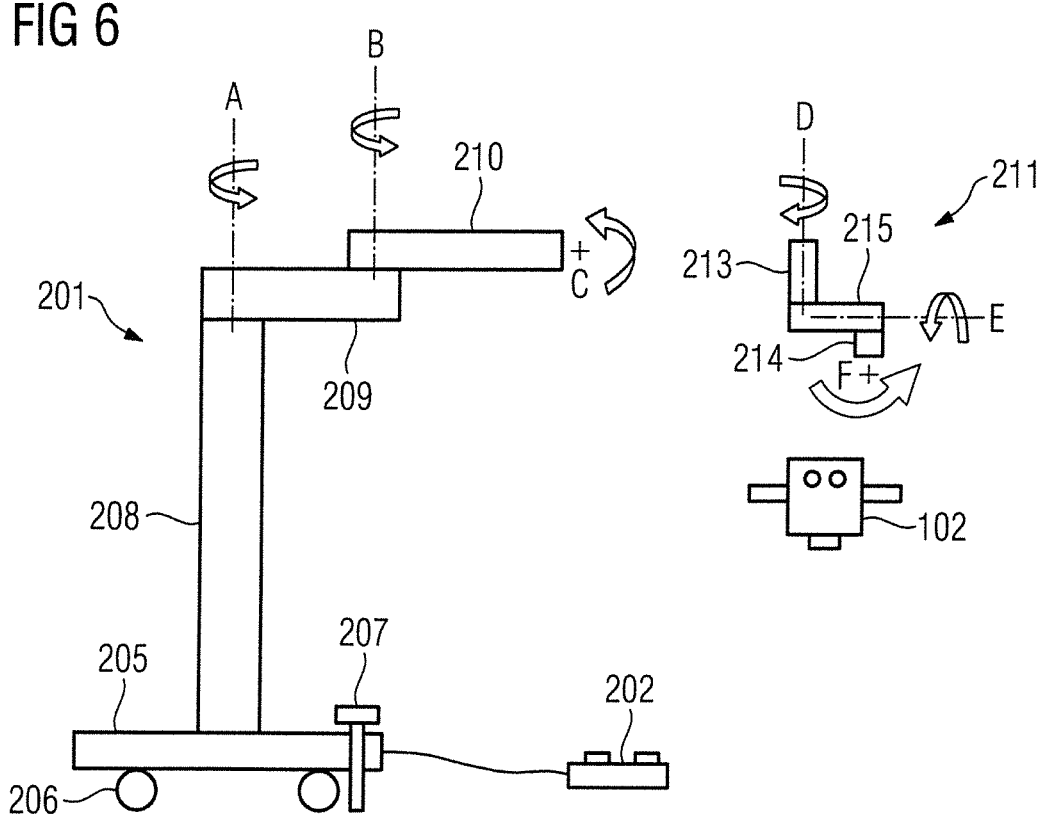

SURGICAL ASSISTANCE SYSTEM

BACKGROUND

1. Field of the Invention

The present invention relates to a surgical assistance system and, in particular, to an assistance system for microsurgery.

2. Description of the Related Art

In surgical interventions and, in particular, in microsurgical interventions and tumor operations, intraoperative tissue samples are taken, which are then analyzed by a pathologist using frozen section diagnosis. The results of this analysis are then relayed to the operating surgeon by telephone and analyzed by the surgeon for the purpose of determining the further course of treatment. In order to perform such a frozen section diagnosis, the tissue samples acquired intraoperatively are sense to a pathology laboratory, where the samples are analyzed. There, the tissue samples are frozen and sectioned before being analyzed by the pathologist. This process generally takes around 15 minutes for one tissue sample. The period of time until the results of the analysis are received increases accordingly if multiple tissue samples are analyzed. Added to this duration is the time required for transporting the tissue samples to the pathology laboratory.

Because the quality of sections acquired from frozen tissue samples is poorer than the quality of sections of formalin-fixed, paraffin-embedded tissues and because only a limited amount of time is available for analysis, the demands on the abilities of the pathologist are very high. However, by the nature of the system, due to the low number of tissue samples, the poor quality of the frozen sections, and the short period of time available for analysis, it is possible for even a very good pathologist to return erroneous analyses relatively frequently, even when experienced pathologists are able to attain accuracy rates of 90% or more.

JP-H07-95556 A discloses a system that allows a remote observer to view an enlarged image of a sample on the stage of a microscope located in the operating room. In addition, the remote observer is connected to the operating room via telephone, such that communication between the treating doctor and the observer is possible.

US 2005/0033556 A1 discloses a diagnostic system comprising a device located in the operating room for acquiring genetic data from patient tissue as well as a diagnostic device located in a different room. The acquired genetic data are sent to the diagnostic device, where a search is performed for diagnostic information and the information found is displayed so that it may be verified by a pathologist. The verified diagnosis is then shown on a display located in the operating room. This allows the time required for a diagnosis to be shortened.

US 2013/0324846 A1 discloses a device and a method for optical pathology. In the method, an optical examination of the tissue is conducted in vivo. To this end, the tissue is first dyed with a fluorescent dye. Then, with the aid of confocal imaging, fluorescence images are obtained on a cellular level and displayed on a monitor. With reference to the images shown, a pathology diagnosis of the tissue is conducted. This monitor may be disposed in a room other than the operating room. An endoscope or a hand-guided microfiber probe may be used to supply the radiation exciting the fluorescence to the tissues to be examined and to record the fluorescence radiation emitting from the tissue. In addition, the device comprises a CCD camera or a CMOS camera by means of which a macroscopic overview of the tissue area in question may be obtained.

Using the devices described in the prior art, a remote pathology diagnosis is possible without the tissue needing to be transported to a pathology laboratory. The pathology diagnosis may then be forwarded to the treating surgeon via a telephone line or a data connection and a display located in the operating room.

With reference to the prior art described above, the object of the present invention is to provide an advantageous surgical assistance system.

SUMMARY OF THE INVENTION

A surgical assistance system according to the invention comprises a group of devices, a pathology unit, and a data connection between the pathology unit and the group of devices. The group of devices comprises at least one endomicroscope for capturing image data at the cellular level of an operating field, an imaging device for capturing overview images of the operating field, and a transmission unit for transmitting the cellular-level image data and/or the overview image data collected. The imaging device for recording overview image data of the operating field is preferably a surgical microscope.

The pathology unit comprises a receiving unit for receiving the cellular-level image data and/or the overview image data as well as a display unit for displaying the received cellular-level image data and/or the received overview image data. The pathology unit is preferably disposed in a different room than the group of devices and typically comprises one or more computers. The transmission unit of the group of devices is connected to the receiving unit of the pathology unit via the data connection between the pathology unit of the group of devices.

In the surgical assistance system according to the invention, the imaging device contains at least one functional unit or at least one functional unit is assigned to the imaging device. Additionally or alternatively, the endomicroscope contains at least one functional unit or at least one functional unit is assigned to the endomicroscope. In addition, a functional control unit is assigned to the respective functional unit for the purpose of controlling the functional unit. Here, the functional control units can each be individual control units or subunits of a common central control unit that is able to control each of the functional units. Moreover, the pathology unit comprises an input unit for inputting functional control data for the at least one functional unit as well as a transmitting unit for transmitting the functional control data to a data receiving unit of the group of devices via the data connection. The data receiving unit of the group of devices is designed to relay the received functional control data to the at least one functional control unit.

In particular, a motor-driven positioning and/or orientation device may be present as a functional unit for positioning and/or orienting the imaging device and/or the endomicroscope. In this case, the functional control data contain positioning and/or orientation data for the imaging device, which is preferably embodied as a surgical microscope, and/or for the endomicroscope.

If the imaging device is embodied as a surgical microscope comprising at least one observation beam path for showing an observation image, at least one of the following units may be present as a functional unit of the surgical microscope:

1. An Image Blending Device Acting on the Observation Beam Path for Overlaying the Observation Image with a Superimposed Display.

When an image blending device is used, the functional control data contain image data of a blended image. This embodiment allows the pathologist to blend information directly into the observation beam path of the surgical microscope. Such data may include, for example, image data for an arrow by means of which the pathologist indicates the location at which a cellular-level microscopic image should be captured by the endomicroscope. Furthermore, the option is available of the pathologist overlaying image data onto the overview image displayed in the display unit of the pathology unit, for example, to mark a tumor location. Here, the overview image acquired using the surgical microscope may be overlaid with, for example, a blended image with demarcation lines showing the position of the tissue to be removed or certain regions of the overview image may be overlaid with the blended image in such a way that, for example, tissue to be removed is indicated by color.

2. A Focusing Unit.

If the focusing unit is used, the functional control data contain focus control data. By accessing the focus of the surgical microscope, the pathologist has the ability to focus the overview image onto a tissue area of interest in order to examine said area in greater detail. Using such an examination, a decision may then be made as to whether a cellular-level microscopic image should be acquired of this area of tissue.

3. A Magnification Adjustment Unit.

If a magnification adjustment unit is used, the functional control data contain magnification adjustment control data. Access to the magnification adjuster of the surgical microscope allows the pathologist to show an area of tissue of interest at the level of magnification desired by the pathologist.

4. A Unit for Generating Fluorescence Stimulation in the Operating Field.

In this case, the functional control data contain control data for controlling the unit for generating fluorescence stimulation. In particular, the unit for generating fluorescence stimulation may be a lighting unit that generates light with a wavelength of approximately 400 nm, for example, by means of a suitable light source, or a dichroic filter that can be pivoted into the beam path of the lighting unit. Such an illumination allows fluorescence data of the tissue to be examined to be captured, for example, by means of the endomicroscope. The pathology diagnosis may then be supported by a cellular-level fluorescence image in addition to a conventional cellular-level image.

5. A Unit for Recording Fluorescence Data.

In this case, the functional control data contain control data for controlling the unit for recording fluorescence data. Here, the unit for recording fluorescence data may be a dichroic filter that is pivotable into the observation beam path and that filters out the stimulation radiation from the observation beam path. In particular, the pivotable dichroic filter may have a filter characteristic that not only filters out stimulation radiation from the illumination beam path but rather allows only the fluorescence beam to pass. This embodiment allows the pathologist to not only record fluorescence data with the endomicroscope but also to receive an overview of the fluorescence in the operating field.

6. A Laser-Doppler Imaging Unit.

If a laser-Doppler imaging unit is used, the functional control data contain control data for controlling the laser-Doppler imaging unit. Using the laser-Doppler imaging unit, the pathologist may, for example, obtain data regarding the blood flow through the tissue to be examined.

7. A Laser Speckle Interferometry Unit.

If laser speckle interferometry is used, the functional control data contain control data regarding the control of the laser speckle interferometry unit. Laser speckle interferometry may be used to acquire movement data such as, for example, data regarding blood flow within the tissue.

8. An Image Capture Device Comprising a Hyperspectral Sensor.

In this case, the functional control data contain control data for controlling the image capture device having a hyperspectral sensor. Such a sensor allows the pathologist to conduct a thorough spectral analysis of the light reflected by the tissue to be examined.

When the imaging device comprises one or more of the functional units listed above, the diagnostic information available to the pathologist is considerably expanded. In particular, when a plurality of the functional units listed above are present, the pathologist has the ability to obtain a comprehensive view of the tissue to be examined. This can considerably reduce the risk of a misdiagnosis.

In an advantageous refinement of the surgical assistance system according to the invention, the group of devices also comprises a device for determining the position and/or orientation data of at least the distal end of the endomicroscope. This device may be either a navigation system or an image processing module of the surgical microscope in which the position data and/or the orientation data of the endomicroscope are determined with reference to at least one image captured by the surgical microscope showing the distal end of the endomicroscope. The navigation system is able to "see" and therefore detect the distal end of a device inserted into the body. The OPMI is generally also able to see the proximal end and therefore indicate its position relative to anatomical landmarks. With the aid of the device for detecting position and/or orientation data, the pathologist may then at any time determine the position and orientation of the endomicroscope relative to the tissue to be examined. The pathologist then has the option of providing the treating surgeon with position data and/or orientation data in the operating field. The pathologist can therefore inform the surgeon in an uncomplicated manner how the endomicroscope must be positioned and/or oriented in order to capture the cellular-level image required for pathological diagnosis. The surgeon can then position and/or orient the endomicroscope with reference to the positioning and/or orientation data received.

In addition, the group of devices of the surgical assistance system can comprise at least one surgical treatment device, with the position and orientation of at least one part of the surgical treatment device being detected by means of the device for determining position and/or orientation data. A positioning and orientation unit is assigned to the surgical treatment device for positioning and orienting at least one part of the surgical treatment device, with a positioning and orientation control unit being assigned to the position and orientation unit for the purpose of controlling the positioning and orientation of the part of the surgical treatment device. The input unit of the pathology unit is then designed for the input of positioning and orientation data for the positioning and orientation control unit. Moreover, the transmission unit of the pathology unit is designed for transmitting the positioning and orientation data via the data connection to the data receiving unit of the group of devices. Finally, the data receiving unit of the group of devices is designed to relay the received positioning and orientation control data to the positioning and orientation unit. In this design of the surgical assistance system according to the invention, the pathologist has the ability to position and orient the surgical treatment device in whatever way the pathologist deems necessary based on the pathology diagnosis. The surgical treatment device may, in particular, be a suction device having a suction tip, said suction tip forming the part of the surgical treatment device, the position and orientation of which are detected. However, other surgical treatment devices such as, for example, surgical lasers, may also come into consideration.

When the pathologist is positioning and/or orienting the endomicroscope, the surgical microscope, or the surgical treatment device, however, it is necessary to ensure that such positioning and/or orientation can only occur when it is approved by the on-site treating surgeon and that the positioning and/or orientation may be interrupted by the surgeon at any time in order to prevent tissue damage in a timely fashion.

Within the framework of the invention, the surgical assistance system may also be designed in such a way that it is able to provide an automated diagnosis. In such a case, the pathology unit comprises a diagnostic database that contains a number of stored diagnoses as well as a number of stored image data and in which each of the number of stored diagnoses is associated with at least one characteristic piece of image data out of the number of stored image data. In addition, the pathology unit then comprises an image analysis unit for the extraction of particular image data from the cellular-level image data and/or overview image data received as well as a diagnostic unit that is connected to the image analysis unit for the purpose of receiving the extracted image data and connected to the diagnostic database for the purpose of receiving the stored image data. On the basis of a comparison of the extracted image data to the received stored image data, the diagnostic unit selects a diagnosis and displays it on the display unit as a suggested diagnosis. This allows a preliminary recommended diagnosis to be quickly provided to the pathologist. If the comparison shows that certain image data match the characteristic image data for multiple diagnoses, a preliminary suggestion of possible diagnoses may be offered to the pathologist. The pathologist is then able in a first step to review the diagnoses offered and either verify or discard them. By pre-selecting possible diagnoses, the time required for preparing the pathological diagnosis may be shortened.

The surgical assistance system according to the invention offers the pathologist a full range of options for influencing the gathering of data and/or providing information to the treating surgeon. As compared to the diagnostic systems known from the prior art, the surgical assistance system according to the invention expands options for cooperation between the pathologist and the treating surgeon.

Here, it should be noted that the image data that may be acquired using the surgical assistance system may also be used for purposes other than sending them to the pathology system in order to obtain a pathology diagnosis. For example, instead of or in addition to a pathologist, another doctor, for example, a specialist in a specific treatment, may be present in the room in which the pathology unit is located in order to assist the surgeon in performing the specialized treatment. It is also possible for a more experienced surgeon to support a less experienced surgeon remotely, for example, by drawing borders on the observation image of a surgical microscope up to which the treating surgeon is allowed to cut. The notation of specific features in the operating field can therefore also occur remotely in a problem-free fashion.

In this sense, the term "pathology system" in the surgical assistance system represents only a designation that does not necessarily imply that a pathology diagnosis is being made with the aid of the pathology system. Rather, the term "pathology system" should be understood to mean that the system provides a doctor located outside the operating room with image data regarding the operating field, with reference to which said doctor is able to acquire useful additional information that can then be relayed to the surgeon.

Additional features, properties, and advantages of the present invention may be found in the description of exemplary embodiments below with reference to the attached drawings.

BRIEF DESCRIPTION OF THE DRAWINGS

FIG. 5 shows a stand with the microscope mounting and a surgical microscope disposed thereon.

FIG. 6 shows the degrees of freedom available to the stand and the mounting shown in FIG. 5.

DETAILED DESCRIPTION

Figure 1:
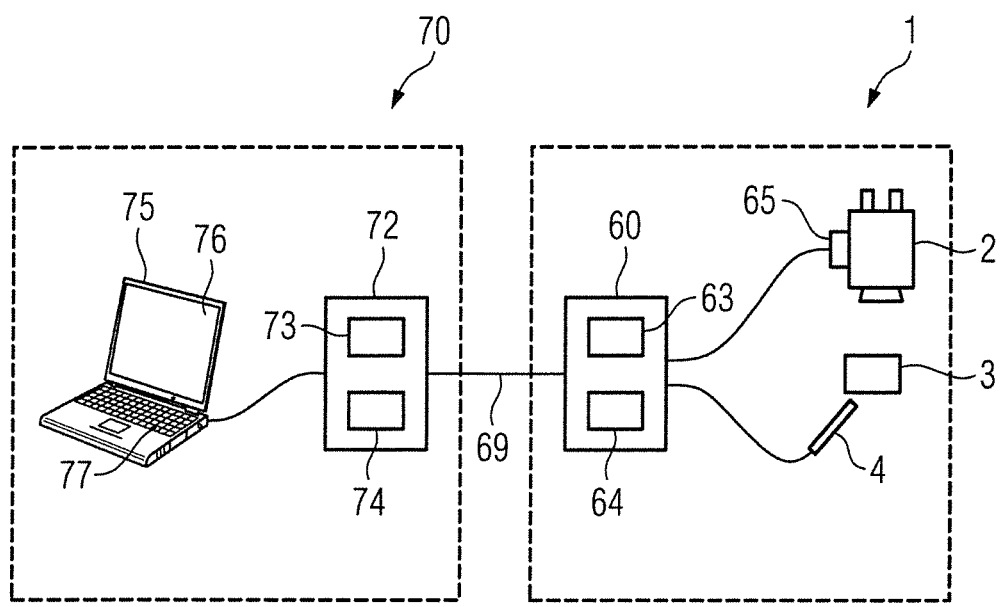
FIG. 1 shows a schematic depiction of a surgical assistance system according to the invention.

A first exemplary embodiment of the surgical assistance system according to the invention will be described below with reference to FIG. 1. FIG. 1 schematically depicts a group of devices 1 located in the operating room as well as a pathology unit 70 that may be located outside the operating room. Typically, the pathology unit 70 is located at a distance from the operating room in a different room of the same building. However, it is also fundamentally possible for the pathology unit to be located in a different building or even in a different city or another country.

The group of devices 1 comprises a surgical microscope 2 by means of which an operating field 3 may be observed. Using the surgical microscope 2, essentially an overview image of the operating field 3 is acquired. Moreover, the group of devices 1 comprises an endomicroscope 4 by means of which cellular-level image data may be captured at selected locations in the operating field 3. The surgical microscope 2 as well as the endomicroscope 4 each comprise an electronic image capture unit by means of which the captured optical images can be converted into electronic images and that are connected to a transmitting and receiving unit 60 belonging to the group of devices 1 and having a transmitter 63 and a receiver 64.

The pathology unit 70 disposed at a distance from the group of devices 1 comprises a transmitting and receiving unit 72 having a transmitter 73 and a receiver 74 as well as a computer 75 that is equipped with a monitor 76 as a display unit for displaying image data and a keyboard 77 for the input of data. Naturally, other devices for the input of data may also be present, although they are not shown here. In particular, for example, interfaces may be considered by way of which data from external devices may be transmitted to the computer 57. As an interface, for example, a USB interface, may be present by way of which a USB stick containing data may be connected to the computer. Drives such as, for example, CD-ROM drives or DVD drives, may also be used to input data stored on data media. The person skilled in the art will also be easily able to recognize other options for the input of data into the computer 75.

The transmitting and receiving unit 72 of the pathology unit 70 is connected to the transmitting and receiving unit 60 of the group of devices 1 via a bidirectional data line.

The fundamental structure of the surgical microscope 2 will be described in the following with reference to FIG. 2.

Figure 2:
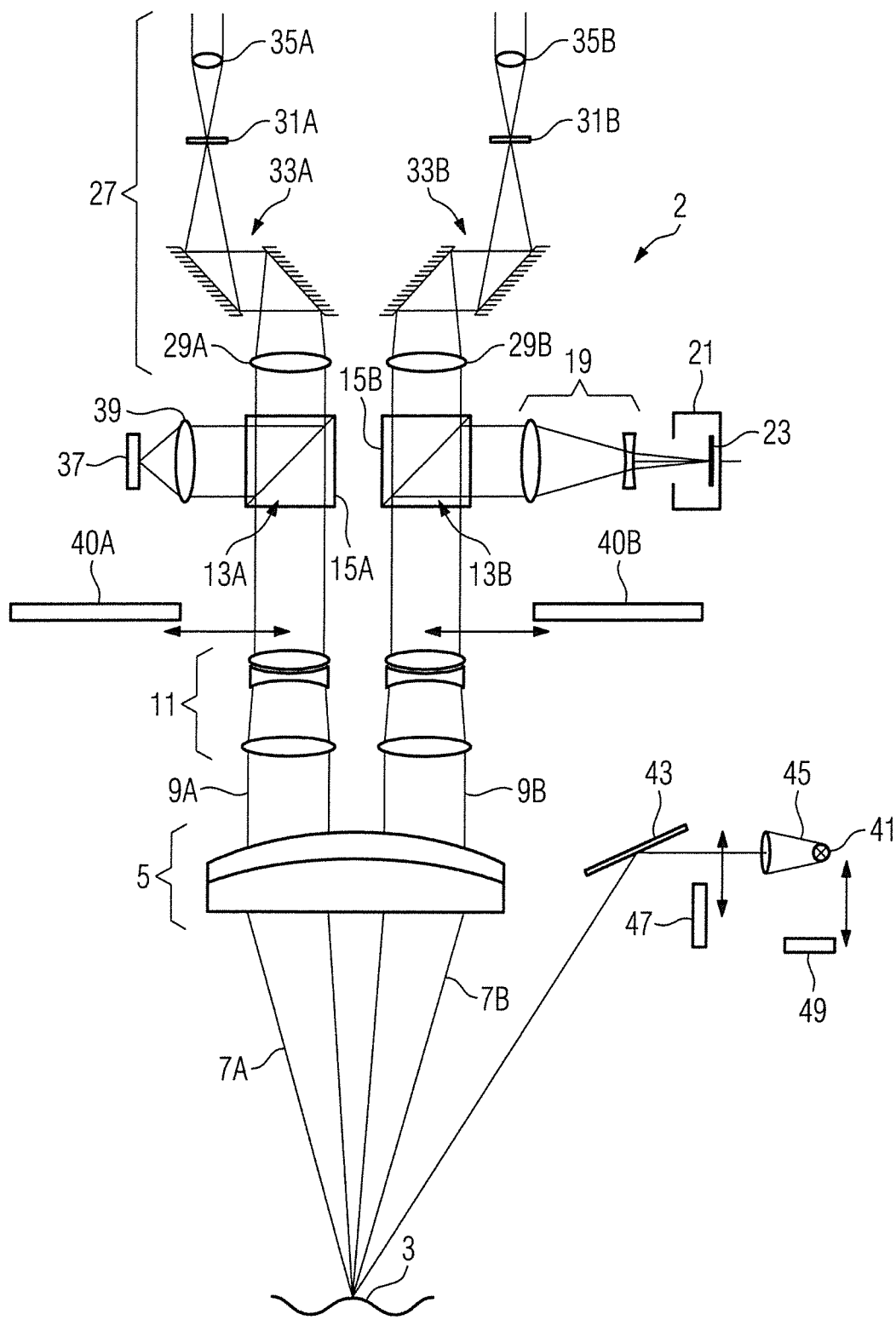
FIG. 2 shows a schematic depiction of the typical structure of a surgical microscope.

The surgical microscope 2 shown in FIG. 2 comprises as its essential components a lens 5 to be directed at an object field 3; said lens may in particular be embodied as an achromatic or apochromatic lens. In the present exemplary embodiment, the lens 5 is comprised of two lens elements cemented to one another to form an achromatic lens. The object field 3 is disposed in the focal plane of the lens 5, such that it is reproduced by the lens 5 to infinity. In other words, a divergent bundle of rays 7 originating from the object field 3 would be converted to a parallel bundle of rays 9 upon passing through the lens 5.

On the observer size of the lens 5, a magnification adjuster 11 is disposed that may be embodied either as a zoom system for the continuous adjustment of the magnification factor, as in the exemplary embodiment shown here, or as a so-called Galilean optical system for the graduated adjustment of the magnification factor. In a zoom system comprised, for example, of a combination of lenses having three lenses, the two object-side lenses may be shifted in order to vary the magnification factor. However, the zoom system can actually also comprise more than three lenses, for example, four or more lenses, in which case the outer lenses may also be disposed in a fixed manner. In a Galilean optical system, on the other hand, a plurality of fixed lens combinations exists representing different magnification factors that can be placed in the beam path in a rotational fashion. A zoom system as well as a Galilean optical system converts an object-side parallel bundle of rays into an observer-side parallel bundle of rays having a different bundle diameter. In the present exemplary embodiment, the magnification adjuster 11 is already a part of the binocular beam path of the surgical microscope 1, i.e., it has its own lens combination for each stereoscopic partial beam path 9A, 9B of the surgical microscope 1. The adjustment of the magnification factor by means of the magnification adjuster 11 occurs in the present exemplary embodiment via a motor-driven actuator that, along with the magnification adjuster 11, is part of a magnification adjustment unit for adjusting the magnification factor.

An interface arrangement 13A, 13B is connected to the magnification adjuster 11 on the observer side, by way of which the external devices can be connected to the surgical microscope 1 and that, in the present exemplary embodiment, comprises beam splitter prisms 15A, 15B. Fundamentally, however, other types of beam splitters may be used as well such as, for example, semi-reflecting mirrors. In the present exemplary embodiment, the interfaces 13A, 13B serve to decouple a bundle of rays from the beam path of the surgical microscope 2 (beam splitter prism 15B) and/or to couple a ray bundle into the beam path of the surgical microscope 2 (beam splitter prism 15A).

In the present exemplary embodiment, the beam splitter prism 15A in the partial beam path 9A, with the aid of a display 37, for example, a digital mirror device (DMD) or an LCD display, and an associated lens 39, serves to superimpose information or data for an observer into the partial beam path 9A of the surgical microscope 1 via the beam splitter prism 15A. In the other partial beam path 9B, a camera adapter 19 with a camera 21 attached thereto is disposed at the interface 13B that is equipped with an electronic image sensor 23, for example, a CCD sensor or a CMOS sensor. Using the camera 21, an electronic and, in particular, digital image of the tissue region 3 may be captured. In particular, a hyperspectral sensor can also be used in which not only three spectral channels (for example, red, green, and blue) are present, but rather a plurality of spectral channels.

A binocular tube 27 is connected to the interface 13 on the observer side. Said binocular tube comprises two tube lenses 29A, 29B that focus the respective parallel bundles of rays 9A, 9B on an intermediate image plane 31, i.e., the observed object 3, on to the respective intermediate image plane 31A, 31B. The intermediate images located in the intermediate image planes 31A, 31B are finally projected again to infinity by ocular lenses 35A, 35B, such that an observer would be able to view the intermediate image with relaxed eyes. Moreover, a magnification between the two bundles of rays 9A, 9B occurs in the binocular tube by means of a mirror system or by means of prisms 33A, 33B in order to adapt said bundles of rays to the distance between the observer's eyes. In addition, image erection occurs by means of the mirror system or the prisms 33A, 33B.

The surgical microscope 2 is additionally equipped with an illumination device by means of which the object field 3 can be illuminated with wideband illumination light. To this end, the illumination device in the present exemplary embodiment comprises a white light source 41, for example, a halogen bulb or a gas discharge lamp. The light emitted by the white light source 41 is directed by a deflecting prism 43 in the direction of the object field 3 in order to illuminate said object field. In addition, an illumination lens 45 is present in the illumination device that ensures even illumination of the entire observed object field 3.

It should be noted here that the illumination beam path shown in FIG. 2 is shown in a highly schematic fashion and does not necessarily reflect the actual course of the illumination beam path. Fundamentally, the illumination beam path may be embodied as a so-called oblique illumination that most closely approximates the schematic depiction in FIG. 2. In the case of such oblique illumination, the beam path runs at a relatively large angle (6° or more) to the optical axis of the lens 5 and can, as shown in FIG. 1, run completely outside of the lens. Alternatively, however, the option also exists of allowing the illumination beam path of the oblique illumination to run through an edge region of the lens 5. Another option for the arrangement of the illumination beam path is so-called 0° illumination in which the illumination beam path extends through the lens 5 and is coupled into the lens between the two partial beam paths 9A, 9B along the optical axis of the lens 5 in the direction of the object field 3. Finally, the option also exists of embodying the illumination beam path as a so-called coaxial illumination in which one first and one second illumination beam path are present. The partial beam paths are coupled into the surgical microscope via one or more beam splitters parallel to the optical axes of the observation partial beam paths 9A, 9B, such that the illumination runs coaxially to the two observation partial beam paths.

In the surgical microscope shown in FIG. 2, influence may be exerted on the illumination. For example, a filter 47 may be placed in the illumination beam path that only allows a narrow spectral range of the broad spectrum of the white light source 41 to pass, for example, a spectral range with which the fluorescence of a fluorescent dye located in the object field 3 may be stimulated. In order to observe the fluorescence, filters 37A, 37B may be placed in the observation partial beam paths that filter out the spectral range used to excite the fluorescence in order to be able to observe the fluorescence.

The illumination device may additionally be equipped with the unit for changing the illumination light source. This is implied in FIG. 2 by a system for exchanging the white light source 41 for a laser 49. Using a laser as the light source, in particular using an infrared laser, allows, for example, the use of laser Doppler imaging or laser speckle imaging in conjunction with a suitable image sensor 23. The unit for changing the illumination light source is motor driven in the present exemplary embodiment and may be controlled from the pathology unit 70 using suitable control data.

In the variant embodiment of the surgical microscope 2 shown in FIG. 2, the lens 5 comprises solely an achromatic lens. However, an objective lens system comprised of a plurality of lenses may also be used, in particular a so-called zoom lens, by means of which the working distance of the surgical microscope 2, i.e., the distance from the object-side focal plane to the apex of the first object-side lens surface of the objective 5, also referred to as the focal distance, may be varied. The zoom lens 50 also reproduces the object field 3 disposed in the focal plane into infinity, such that a parallel bundle of rays is present on the observer side.

Figure 3:
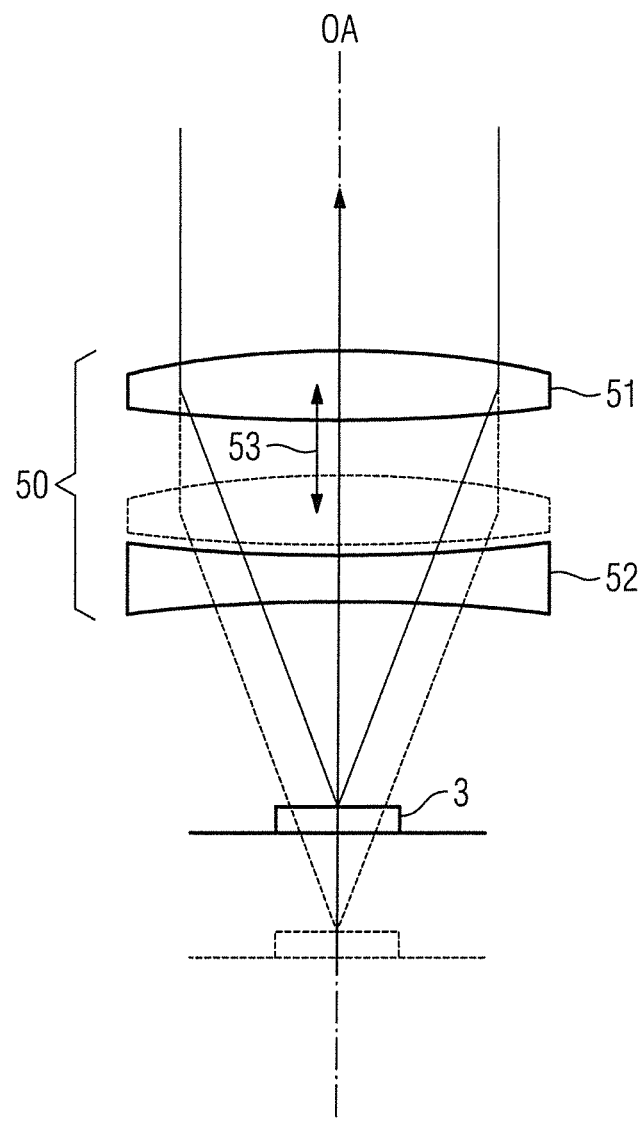
FIG. 3 shows a lens for a surgical microscope that may be used in place of the lens shown in FIG. 2.

One example of a zoom lens is shown schematically in FIG. 3. The zoom lens 50 comprises a positive member 51, i.e., an optical element having positive refraction shown schematically in FIG. 3 as a convex lens. Moreover, the zoom lens 50 comprises a negative member 52, i.e., an optical element having negative refraction, which is shown in FIG. 3 as a concave lens. The negative member 52 is located between the positive member 51 and the object field 3. In the zoom lens 50 shown here, the negative member 52 is disposed in a fixed manner whereas the positive member 51, as implied by the double arrow 53, is disposed in a displaceable fashion along the optical axis OA. When the positive member 51 is slid into the position shown by dashed lines in FIG. 3, the focal length is extended such that the working distance of the surgical microscope 2 from the object field 3 is changed.

Although the positive member 51 is embodied in a displaceable fashion in FIG. 3, the fundamental possibility also exists of disposing the negative member 52 rather than the positive member 51 in a movable fashion along the optical axis OA. However, the negative member 52 frequently forms the terminal line of the zoom lens 50. A fixed concave lens therefore offers the advantage that the interior of the surgical microscope 2 is easier to seal off from outside influences. Moreover, it should be noted that, although the positive member 51 and the negative member 52 are shown merely as individual lenses in FIG. 3, each of these lenses may take the form of a group of lenses or a cemented element rather than an individual lens, for example, in order to design the zoom lens in an achromatic or apochromatic fashion.

The surgical microscope 2 is connected to a functional control unit 65. Said functional control unit comprises a plurality of functional control subunits by way of which the functions of the surgical microscope 2 may be controlled. For example, the functional control subunits may be used to adjust the position of the zoom system 11 for adjusting the magnification factor of the surgical microscope, the position of the filters 37A, 37B, and 47 in order to allow the observation of the fluorescence, the type of light source 41, 49 used so as to allow laser Doppler imaging or laser speckle imaging, etc. If the surgical microscope 2 is equipped with a zoom lens, the working distance between the surgical microscope and the object field 3 may also be adjusted with the aid of a functional control subunit of the functional control unit 65.

The surgical assistance system according to the invention allows images captured by the surgical microscope 2 and the endomicroscope 4 to be sent to the pathology unit 70 with the aid of the transmission unit 63 of the transmitting and receiving unit 60 of the group of devices 1. There, the transmitted image data are received by the receiving unit 74 and relayed to the computer 57 for display on the monitor 76. A pathologist is then able to view the images on the monitor and prepare a pathology diagnosis. By virtue of the fact that a bidirectional data connection 69 is present between the transmitting and receiving unit 60 of the group of devices 1 and the transmitting and receiving unit 72 of the pathology system 70, the pathologist is able to send instructions, data, and information to the group of devices 1. This may include, for example, functional control data that act on the display 37 of the surgical microscope 2 in order to superimpose instructions, data, or information into the observation beam path of the surgical microscope 2. Such instructions, data, or information may, for example, be text data by means of which the surgeon may be sent instructions, for example, for positioning the surgical microscope or the endomicroscope. However, instead of being sent as text (or in addition to text instructions), the instructions or information may also be sent in the form of an arrow by means of which the position where additional images should be captured with the aid of the endomicroscope can be indicated in the observation field. The treating surgeon is then able to position the endomicroscope in a precise fashion. This can be significant, for example, if the pathologist requires additional images of certain areas of tissue in order to provide a pathology diagnosis. If the pathologist has already provided a pathology diagnosis, the possibility also exists of marking the areas of tissue that must be surgically removed, for example, by reflecting such markings appropriately into the observation beam path. This can occur, for example, in that the pathologist establishes the outlines of the tissue to be removed using the overview image shown on the monitor 76 and then said outlines being relayed in the form of functional control data comprising data regarding the outlines to the functional control unit 65. The functional control unit then uses the received data to control the image shown on the display 37. However, rather than using outlines, the pathologist can also indicate tissue to be removed by overlaying the areas of the overview image in question with color images that show the tissue to be removed in a color-coded fashion. In such a case, the functional control data sent to the functional control unit 65 would then contain image data of the color overlay images. Naturally, the possibility also exists of displaying the data sent by the pathologist on a monitor in the operating room in addition to or as an alternative to reflecting the data into the observation beam path of the surgical microscope.

In addition to the transmission of information to the treating surgeon using image data, the possibility also exists of transmitting audio data to the group of devices 1 insofar as said group of devices comprises a speaker. In such a case, it is advantageous for the group of devices 1 to comprise a microphone such that the treating surgeon and the pathologist are able to speak to one another directly.

If the pathologist requires additional image data in order to make a diagnosis, in addition to giving instructions to the surgeon, the pathologist also has the option of directly accessing functions in a remote fashion, for example, of the surgical microscope 2, in order to adjust the magnification of the overview image, for example, or activate or deactivate the various viewing modes such as, for example, fluorescence spectroscopy, laser Doppler imaging, or laser speckle imaging. The pathologist also has the option of remotely adjusting the working distance of the surgical microscope 2.

With the aid of the surgical assistance system, the pathologist is able to very quickly conduct diagnoses on the basis of images captured intraoperatively, in particular because the endomicroscope 4 allows for the capture of cellular-level images. The pathologist is able to be given an orientation of the object field 3 with reference to the overview image acquired by means of the surgical microscope 2. In this manner, the pathologist not only has the ability to provide a pathology diagnosis of a certain tissue but also to take into account the location of the diagnosed tissue in the operation field 3. By capturing additional data such as, for example, fluorescence data, laser Doppler data, laser speckle data, etc., a far more extensive range of data is available than would be the case with frozen section diagnostics or the systems from the prior art described the outset, which additionally allows other specialized doctors such as, for example, radiologists, neurologists, etc., to be consulted in the assessment of the tissue. The surgical assistance system thus allows for real-time consultation between the treating surgeon and a pathologist located at a remote location and/or specialized doctors located at a remote location, with essentially the same image information being available to all participating doctors. In addition, using controlling interventions, the participating doctors are each able to acquire the image data that they need for their diagnoses.

Figure 4:
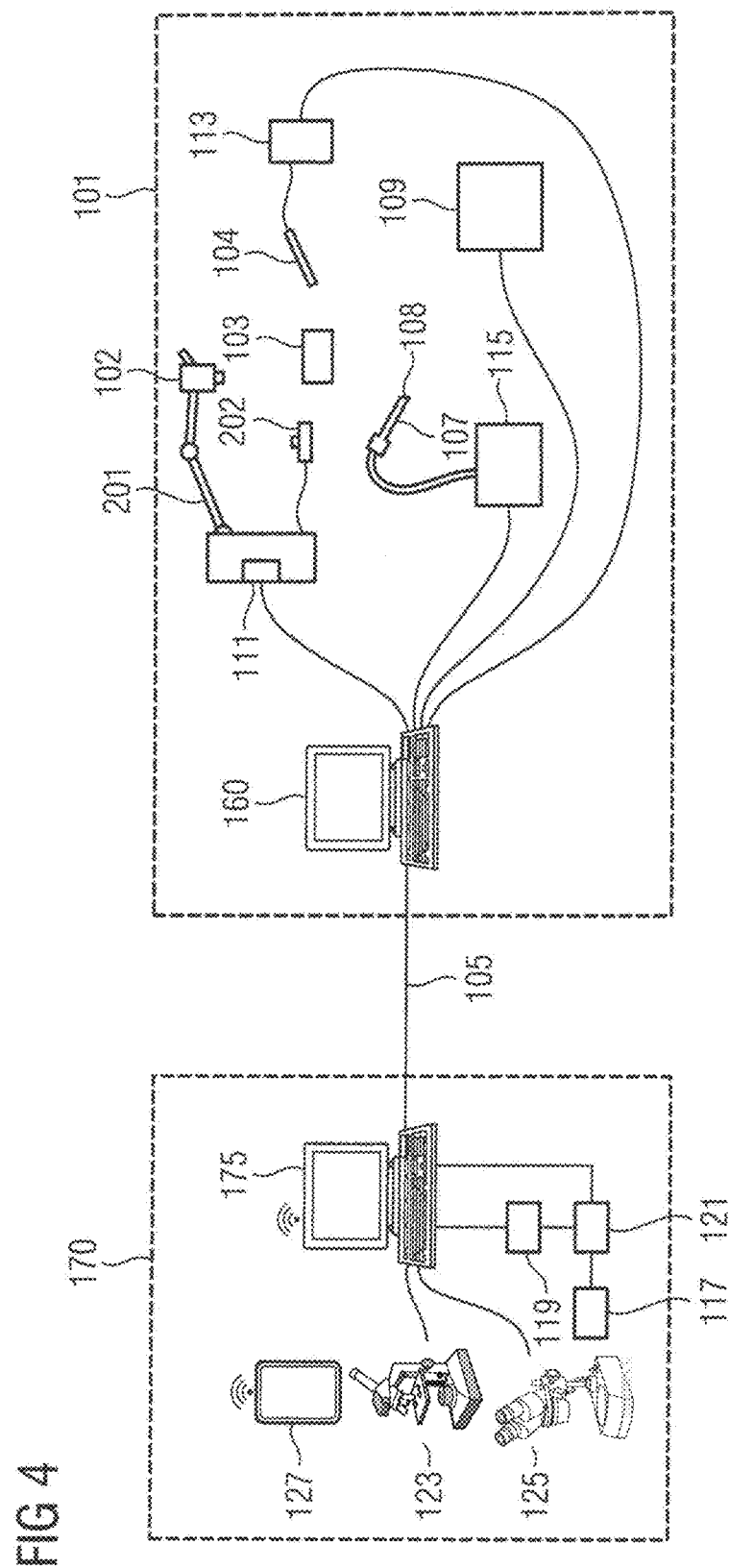
FIG. 4 shows a second exemplary embodiment of the surgical assistance system according to the invention.

A second exemplary embodiment of a surgical assistance system according to the invention is shown in FIG. 4.

The second exemplary embodiment of the surgical assistance system differs from the first exemplary embodiment primarily in that the number of devices in the group of devices has been increased and in that the transmitting and receiving unit of the group of devices as well as the transmitting and receiving unit in the pathology unit are each integrated into a computer 160 and 175, respectively. The two computers 160, 175 are connected to one another via a bidirectional data line 105. Moreover, in the second exemplary embodiment, the pathology unit has also been enhanced with additional functionalities.

The group of devices 101 of the second exemplary embodiment also comprises, in addition to a surgical microscope 102 and an endomicroscope 104 for acquiring an overview image and a cellular-level image, respectively, from an object field 103, a surgical suction device 107 and a navigation system 109. Using the navigation system 109, the position data and, optionally, the orientation data of the surgical microscope 102, the tip of the endomicroscope 104, and the tip 108 of the suction device 107 can be detected relative to the object field. The image data captured by the endomicroscope 104 or by the surgical microscope 102 can then be provided with coordinates with reference to which a position and, optionally, also an orientation relative to the object field 103 can be determined. These data are then transmitted along with the overview image acquired using the surgical microscope 102 and/or along with the cellular-level image acquired by means of the endomicroscope 104 to the pathology unit 170, where, for example, they can be blended into the respective image. This allows the coordinates of the tip of the endomicroscope 104 to be indicated on the overview image such that the location of the images captured on the cellular level is marked on the overview image. In addition, this allows new positions at which, for example, cellular-level images should be captured to be sent to the treating surgeon in the form of navigation data.

In the present exemplary embodiment, the surgical microscope 102 is additionally attached to a motor-driven stand 201. By the input of navigational data, the surgical microscope 102 can therefore be automatically adjusted in terms of its orientation and its position, which allows the surgical microscope 102 also to be positioned and/or oriented in a remote fashion such that a certain section of the object field 103 is optimally displayed. To this end, a functional control unit 111 is associated with the stand 201 that performs the positioning and/or orientation of the surgical microscope 102 based on the positioning and/or orientation control data received by means of suitable actuators. Positioning and/or orientation data can be received by the functional control unit 111 either from the computer 160 located in the operating room 160 or from the pathology unit 170. The stand 201 and the degrees of freedom allowed by the stand for the surgical microscope 102 will be described in greater detail below with reference to FIGS. 5 and 6.

In the example of the stand 201 shown in FIG. 5, the stand rests on a stand foot 205, on the bottom of which rollers 206 are present that allow the stand 201 to be moved. In order to prevent any undesired motion by the stand 201, the stand foot 205 additionally comprises a foot brake 207.

The actual stand 201 comprises as stand members a height-adjustable stand column 208, a supporting arm 209, a spring arm 210, and an endomicroscope mounting bracket 211, which in turn comprises a connector element 213, a pivot arm 215, and a retaining bracket 214. The degrees of freedom that the stand members provide for positioning the surgical microscope 102 are shown in FIG. 6. The supporting arm 209 is connected on its one end to the stand column 208 in a rotational fashion around an axis A. On the other end of the supporting arm 209, one end of the spring arm 210 is disposed in a rotational fashion around an axis B that is parallel to the axis A, such that the supporting arm 209 and the spring arm 210 form an articulated arm. The other end of the spring arm 210 is formed by a tilt mechanism (not shown) to which the microscope mounting bracket 211 is attached and that allows the microscope mounting bracket 211 to be tilted around the axis C.

The microscope mounting bracket 211 comprises a rotational axis D, a pivot axis E, and a tilt axis F around which the microscope 102 can be rotated, pivoted, and/or tilted. Using a connector element 213, the microscope mounting bracket 211 is attached at the outer end of the spring arm 210 in a rotational fashion around the rotational axis D. The rotational axis D extends along the connector element 213. A pivot arm 215 is joined to the connector element 213, with the aid of which the microscope 102 or, more precisely, a retaining bracket 214 attached to the pivot arm 215 to which the microscope 102 is attached by means of a microscope bracket (not shown), can be pivoted around the pivot axis E. The pivot axis E extends through the pivot arm 215. The angle between the pivot arm 215 and a connector element 213, i.e., the angle between the pivot axis E and the rotational axis D, is variable by means of an adjustment mechanism disposed between the connector part 213 and the pivot arm 215.

The tilt axis F runs through the retaining bracket 214 perpendicular to the viewing plane, allowing the surgical microscope 102 to be tilted. The surgical microscope 102 is attached to the retaining bracket 214 by means of a microscope bracket, which is not shown.

The degrees of freedom of the microscope suspension 211 as well as the adjustment options of the surgical microscope 102, for example, focus, sharpness, magnification factor, etc., are adjustable via controlling equipment 202 which, in the present exemplary embodiment, is depicted as a foot control switch. However, it may also be embodied as a hand switch element or is a combination of the two. Remote control by the pathology unit is possible as well.

In order to prevent an undesired movement of the microscope 102 from a selected position, the stand members and the joints between the stand members are provided with brakes (not shown) that are fixed into place after the positioning of the microscope 102. Manual and electrically activated brakes may be considered for the brakes.

Even if the stand 201 has been described with reference to a concrete example, the person skilled in the art will note that other kinds of stands may be used as well. Likewise, it is also possible for the endomicroscope 104 and/or the suction device 107 to also be attached to a motor-driven stand such that the device in question can be positioned and/or oriented with reference to position control data and/or orientation control data.

In the present exemplary embodiment, a functional control unit 113 is assigned to the endomicroscope 104, by means of which functions of the endomicroscope 104, for example, the type of illumination, may be adjusted with reference to suitable functional control parameters. If the endomicroscope 104 is disposed on a motor-driven stand, the option additionally exists of positioning and/or orienting the distal end of the endomicroscope 104 relative to the object field 103 via the functional control unit with reference to positioning and/or orientation data. Here, however, it must be ensured that no damage to the tissue in the object field 103 occurs if the positioning occurs by means of a motor. Positioning should therefore only be possible with the permission of the treating surgeon and supervised by said surgeon. Here, the surgeon must always have the option of overriding a remote positioning originating from the pathology unit 170 such that the surgeon can interrupt the automatic positioning at any time as needed.

According to the second exemplary embodiment, the group of devices 101 of the surgical assistance system also comprises a surgical suction device 107, for example, for the removal of tumors. The position of the suction tip 108 of the suction device 107 can be tracked with the aid of the navigation system 109. In addition, the option is available of controlling the position of the suction tip 108 from the pathology system 170 by means of positioning and/or orientation data. These data are then relayed to a functional control unit 115 that allows the positioning and/or orientation of the suction tip 108 relative to the object field 103 by means of a suitable motor-driven stand.

As has already been mentioned above, in the present exemplary embodiment, the transmitting and receiving unit of the group of devices 101 is disposed in a computer 160 located in the operating field by means of which functional control data can also be sent to the respective functional control units and/or functional control subunits from the operating room. In addition, the presence of the computer 160 and the operating room allows for its monitor to show the precise image available to the pathologist on the monitor 176 of the computer 175 in the pathology unit.

In the present exemplary embodiment, the transmitting and receiving unit is located in a computer 175 in the pathology system 170 as well. In addition, the pathology unit 170 of the present exemplary embodiment comprises a diagnostic database 117, an image analysis unit 119, and a diagnostic unit 121. The image analysis unit 119 is connected to the receiving unit of the pathology system 170 in order to receive the cellular-level image data and the overview image data. The image analysis unit serves to extract certain image information from the cellular-level image data received and/or the overview image data received. For example, if the cellular-level image data and/or the overview image data contain fluorescence images, the image analysis unit 119 can serve to find locations with characteristic fluorescence radiation. If a hyperspectral sensor is used for capturing the images, another option lies in the extraction of certain spectral characteristics.

The diagnostic unit 121 is connected to the image analysis unit 119 in order to receive the extracted image information. The diagnostic unit is additionally connected to the diagnostic database 117 that contains a plurality of stored diagnoses and a plurality of stored image data. In the diagnostic database 117, each diagnosis is associated with at least one stored piece of image data characteristic of the respective diagnosis. The diagnostic unit 121 then compares the characteristic image information data from the diagnostic database 117 to the image information extracted from the image data. If the comparison of the extracted image data shows a correlation with the characteristic image information from the diagnostic database 117, the diagnostic unit 121 provides the diagnosis associated with the characteristic image information as a suggested diagnosis on the monitor 176. The pathologist now has the option of verifying this diagnosis or discarding it. If the diagnosis is discarded, the pathologist prepares a new diagnosis with reference to the cellular-level images and the overview image. If necessary, using the real-time connection between the operating room and the room in which the pathology system is located, the surgeon and pathologist can cooperate to determine the location from which a conventional tissue sample will be taken. Therefore, if a pathological diagnosis is not possible with reference to the cellular-level image in conjunction with the overview image, the possibility still remains for the pathologist to specify with reference to the overview image where a sample should be taken from. In this manner, the probability of an accurate diagnosis being made using a frozen section is increased. If the room in which the pathology system is located is not located at a very great distance from the operating room, the tissue thus acquired may be sent to the pathologist. For the further investigation of the tissue, it is advantageous for the pathology system 170 to comprise connections for additional devices such as, for example, a conventional light optical microscope 123 or a conventional laser scan microscope 125 as an in vitro diagnosis system. The alternative option also exists of setting up such in vitro diagnostic systems in a room adjacent to the operating room and sending the image data thus acquired to the pathology system via the data line. In such a case, the transport time for the tissue is eliminated because the tissue need not be transported to the pathologist.

In the surgical assistance system according to the second exemplary embodiment, the pathologist may, for example, send navigation data to the functional control unit 115 of the surgical suction device 107 that reflect the detected tumor locations. These locations can then be approached by means of a motorized stand. However, they may also be approached by hand, with the current positions being blended into the observation beam path, for example, by means of the blending unit of the surgical microscope 102. The surgeon is then able to position the suction tip 108 of the surgical suction device 107 in such a way that its position overlaps with the indicated coordinates. Additionally or alternatively, the option also exists of visually blending the position and orientation of the suction tip 107 as it must be positioned and oriented into the observation beam path in order to suction away the tumor cells rather than using coordinates. The surgeon is then able to position the suction tip 108 to overlap with the blended image.

If preoperative data are available and intraoperative data differ from the preoperative data, for example, due to tissue movements such as so-called brain shift, the tumor locations determined by the pathologist can also be used to update the preoperative data, i.e., to correct a shifting of the tissues occurring during the operation (for example, brain shift).

The option also exists of the pathologist remotely selecting a suitable illumination in order to increase the visibility of the tumor locations. Fluorescence stimulation may be considered for this purpose if the tumor emits fluorescent light at a different intensity than healthy tissue.

The pathology system 170 can also comprise a portable computer or tablet 127 on which the cellular-level image data received and/or the overview image data received may be shown. In such a case, the pathologist need not necessarily be at the location of the pathology system 170 if the pathology system is connected, for example, via a wireless connection, to the portable computer or tablet 127. In particular, the option also exists for the pathology system 170 to comprise only the portable computer or tablet 127 as the monitor and input unit. Additional functions of the pathology unit 170 such as, for example, the transmission unit and the receiving unit and, optionally, the diagnostic database 117, the image analysis unit 119, and the diagnostic unit 121, may then be stored in a server. In addition, the option is available of using a far-flung team of doctors as advisors if the pathology system 170 comprises a plurality of tablets 127 to which the server of the pathology system 170 provides the image data requested by the respective doctor.

The present invention has been described with reference to two exemplary embodiments for illustrative purposes. However, it is clear to the person skilled in the art that deviations from these exemplary embodiments are possible. For example, the diagnosis can also fundamentally be made solely with reference to the diagnostic database, the image analysis unit, and the diagnostic unit. In such a case, the pathology system may also be disposed inside the operating room. In addition, the surgical microscope can also comprise more than one image blending device. Here, for example, it is desirable for not only one of the two stereo channels to be provided with an image blending device, but rather for both stereo channels to be provided therewith. This allows stereoscopic image data to be coupled into the observation beam path, which can be particularly advantageous if such image data are to be consulted for positioning a surgical device or the endomicroscope. If, for example, as a positioning aid, an image of the device is to be placed in the position and orientation into which it will be placed blended into the observation beam path and positioning occurs with reference to bringing the real device into conjunction with the blended image, a stereoscopic blending of the image is advantageous. Likewise, the option exists of an image for the pathologist being decoupled not only from one stereoscopic partial beam path but rather from both stereoscopic partial beam paths. The pathologist is then able to obtain a stereoscopic image of the object field. As a display upon which the image is shown, for example, a head-mounted display may be provided. In this manner, the pathologist may be provided with precisely the same image provided to the surgeon upon viewing the surgical microscope. In addition, the option also exists of designing the surgical microscope in a fully digital fashion, i.e., providing two image sensors instead of an optical view into the surgical microscope and displaying the image to the surgeon by means of an electronic view or a head-mounted display. In such a case, a beam decoupling for generating the overview image for the pathologist may be omitted because this image can be generated using the image sensors by means of which the image is captured for the surgeon. The optical device for the reflection of data can also then be omitted in such a case because the data transmitted by the pathologist can be electronically blended into the image provided by the surgeon. Moreover, the group of devices may, additionally or alternatively, comprise other devices not shown in the exemplary embodiments. For example, it would be conceivable for the group of devices to comprise a treatment laser for the coagulation of tissue or for performing sections in addition to or as an alternative to the suction tip. In addition, the option is available of omitting the navigation system and ascertaining the location at which, for example, the tip of the endomicroscope or the suction tip is located using image data captured by the surgical microscope. A suitable system for this purpose is disclosed, for example, in US 2011/0178395 A1, to the contents of which reference is made here with regard to determining the positioning data from the image data of the surgical microscope. The present invention should therefore not be limited to combinations of features of the exemplary embodiments described here, but rather solely limited by the content of the appended Claims.

LIST OF REFERENCE CHARACTERS

1 Group of devices
2 Surgical microscope
3 Operating field
4 Endomicroscope
5 Lens
7 Divergent bundle of rays
9 Bundle of rays
9A, 9B Stereoscopic partial beam path
11 Magnification adjuster
13A, 13B Interface arrangement
15A, 15B Beam splitter prism
19 Camera adapter
21 Camera
23 Image sensor
27 Binocular tube
29A, 29B Tube lens
31A, 31B Intermediate image plane
33A, 33B Prism
35A, 35B Ocular lens
37 Display
39 Lens
40A, 40B Spectral filter
41 White light source
43 Deflection mirror
45 Illumination lens
47 Spectral filter
49 Laser
50 Zoom lens
51 Positive member
52 Negative member
53 Displacement path
60 Transmitting and receiving unit
63 Transmitting unit
64 Receiving unit
65 Functional control unit
69 Data connection
70 Pathology unit
72 Transmitting and receiving unit 73 Transmitting unit
74 Receiving unit
75 Computer
76 Monitor
77 Keyboard
101 Group of devices
102 Surgical microscope
103 Object field
104 Endomicroscope
105 Bidirectional data line
107 Surgical suction device
108 Suction tip
109 Navigation system
111 Functional control unit
113 Functional control unit
115 Functional control unit
117 Diagnostic database
119 Image analysis unit
121 Diagnostic unit
123 Light optical microscope
125 Laser scan microscope
127 Tablet
201 Stand
202 Foot control switch
205 Stand foot
206 Roller
207 Foot brake
208 Stand column
209 Supporting arm
210 Spring arm
211 Microscope mounting bracket
213 Connector element
214 Retaining bracket
215 Pivot arm

What is claimed is:

1. A surgical assistance system comprising:
a group of devices having:
an endomicroscope configured to capture cellular-level image data of an operating field;
a microscope device configured to capture overview image data of the operating field; and
a first transmitter configured to transmit at least one of the cellular-level image data and the overview image data;
a first receiver configured to receive functional control data for control of the group of devices;
a pathology unit comprising:
a second receiver configured to receive the at least one of the cellular-level image data and the overview image data from the first transmitter;
a display unit configured to display the at least one of the cellular-level image data and the overview image data;
an input device configured to receive one or more inputs for entering the functional control data; and
a second transmitter configured to transmit the functional control data to the first receiver for control of the group of devices, the functional control data including the instructions, data, or information; and
a data connection between the pathology unit and the group of devices by way of which the first transmitter and the first receiver of the group of devices are connected to the second receiver and the second transmitter of the pathology unit.

2. The surgical assistance system of claim 1, further comprising a stand with actuators configured to perform at least one of positioning and orienting at least one of the microscope device and the endomicroscope, and the functional control data includes at least one of positioning and orientation control data for at least one of the microscope device and the endomicroscope.

3. The surgical assistance system of claim 1, wherein the microscopic device is a surgical microscope including at least one observation beam path configured to depict an observation image.

4. The surgical assistance system of claim 3, wherein the microscopic device further includes a display configured to superimpose instructions, data, or information into the observation beam path.

5. The surgical assistance system of claim 3, further comprising a focusing unit assigned to the surgical microscope, and the functional control data includes focusing control data.

6. The surgical assistance system of claim 3, further comprising a magnification adjustment unit assigned to the surgical microscope, and the functional control data includes magnification adjustment data.

7. The surgical assistance system of claim 3, wherein the surgical microscope comprises at least one of a light source and a dichroic filter configured to generate fluorescence stimulation in the operating field, and the functional control data includes control data configured to control the at least one of the light source and the dichroic filter for generating fluorescence stimulation.

8. The surgical assistance system of claim 3, wherein the surgical microscope comprises a dichroic filter and the functional control data includes control data configured to control the dichroic filter.

9. The surgical assistance system of claim 3, wherein the surgical microscope comprises a laser-Doppler imaging unit and a unit for laser speckle interferometry and an image capture device comprising a hyperspectral sensor and the functional control data includes control data for at least one of controlling the laser-Doppler imaging unit, control data configured to control the unit for laser speckle interferometry and control data configured to control the image capture device.

10. The surgical assistance system of claim 1, further comprising an image processing module configured to determine position data and orientation data of the endomicroscope based on at least one image captured by the microscope device and containing a distal end of the endomicroscope.

11. The surgical assistance system of claim 10, wherein:
the group of devices comprises at least one surgical treatment device, and position and orientation of at least one part of the surgical treatment device is determined by the image processing module,
motor-driven stand configured to position and orient at least one part of the surgical treatment device, and
the functional control data includes positioning and orientation control data for positioning and orientating the motor-driven stand.

12. The surgical assistance system of claim 11, wherein the surgical treatment device is a surgical suction device having a suction tip forming the at least one part of the surgical treatment device whose position and orientation are captured.

13. The surgical assistance system of claim 1, wherein the pathology unit comprises:
a diagnostic database that contains a number of stored diagnoses and a number of stored image data and in which each of the number of stored diagnoses is associated with at least one characteristic piece of image data for the respective diagnosis out of the number of stored image data, and a computer configured to extract certain image information out of at least one of the cellular-level image data received and the overview image data received, and to receive the stored image information and the associated stored diagnoses, and which, on the basis of a comparison between the extracted image information and the stored image information received, is configured to select a diagnosis and display said diagnosis as a suggested diagnosis on the display unit.

* * * * *